(12) United States Patent
Murayama et al.

(10) Patent No.: US 10,765,852 B2
(45) Date of Patent: Sep. 8, 2020

(54) VALVE BODY, PROCESS FOR PRODUCING THE VALVE BODY, AND MEDICAL INSTRUMENT INCLUDING THE VALVE BODY

(71) Applicant: TERUMO KABUSHIKI KAISHA, Shibuya-ku, Tokyo (JP)

(72) Inventors: Hiraku Murayama, Shizuoka (JP); Yuuki Yoshifusa, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1010 days.

(21) Appl. No.: 15/216,245

(22) Filed: Jul. 21, 2016

(65) Prior Publication Data

US 2016/0361530 A1  Dec. 15, 2016

Related U.S. Application Data

(60) Division of application No. 12/838,017, filed on Jul. 16, 2010, now abandoned, which is a continuation of
(Continued)

(30) Foreign Application Priority Data

Jan. 18, 2008 (JP) ................................ 2008-009725

(51) Int. Cl.
*A61M 39/06* (2006.01)
*B05D 5/08* (2006.01)

(52) U.S. Cl.
CPC ............... *A61M 39/06* (2013.01); *B05D 5/08* (2013.01); *A61M 2039/068* (2013.01);
(Continued)

(58) Field of Classification Search
CPC ............................................... A61M 2039/068
See application file for complete search history.

(56) References Cited

U.S. PATENT DOCUMENTS 4,610,665 A   9/1986   Matsumoto et al.
5,207,656 A   5/1993   Kranys
(Continued)

FOREIGN PATENT DOCUMENTS

EP   0 771 574 A1   5/1997
JP   2-000949 B2    1/1990
(Continued)

OTHER PUBLICATIONS

Office Action (Communication pursuant to Article 94(3) EPC) dated Dec. 19, 2017, by the European Patent Office in corresponding European Patent Application No. 09702835.1. (4 pages).
(Continued)

*Primary Examiner* — Cachet I Proctor
(74) *Attorney, Agent, or Firm* — BUCHANAN INGERSOLL & ROONEY PC

(57) ABSTRACT

A valve body, e.g. a valve body adapted to be disposed in a connector to be connected to a catheter, has an opening/closing part which opens upon inserting a member into the opening/closing part and which closes upon withdrawing the member from the opening/closing part. The valve body includes a main body part made of a silicone rubber and a surface layer disposed on a surface of the main body part. This surface layer serves as a sliding surface which, when a guide wire has been inserted into the opening/closing part, slides on the guide wire. The surface layer is constituted mainly of silicon oxide and hence improves the sliding properties of the guide wire. Thus, the valve body is reduced in the resistance of sliding on the guide wire.

15 Claims, 8 Drawing Sheets

Related U.S. Application Data application No. PCT/JP2009/050516, filed on Jan. 16, 2009.

(52) U.S. Cl.
CPC ..... *A61M 2207/10* (2013.01); *B05D 2203/30* (2013.01); *B05D 2601/00* (2013.01); *Y10T 29/49405* (2015.01)

(56) References Cited

U.S. PATENT DOCUMENTS

| | | | |
|---|---|---|---|
| 5,538,505 A | | 7/1996 | Weinstein et al. |
| 5,749,861 A | * | 5/1998 | Guala ................ A61M 39/26 251/149.1 |
| 6,127,320 A | * | 10/2000 | van Ooij ............ A61M 39/045 508/138 |
| 6,280,399 B1 | | 8/2001 | Rossin et al. |
| 6,334,761 B1 | * | 1/2002 | Tai ...................... F04B 43/043 137/852 |
| 6,866,656 B2 | * | 3/2005 | Tingey ................ A61L 29/085 604/256 |
| 2004/0006330 A1 | * | 1/2004 | Fangrow, Jr. ......... A61M 39/02 604/533 |
| 2004/0086689 A1 | * | 5/2004 | Takahashi ................ C23C 4/02 428/141 |
| 2004/0106942 A1 | * | 6/2004 | Taylor ................ A61B 17/3462 606/185 |
| 2007/0009429 A1 | | 1/2007 | Simon |
| 2007/0125702 A1 | | 6/2007 | Ramaswamy et al. |
| 2008/0234637 A1 | | 9/2008 | McConnell et al. |

FOREIGN PATENT DOCUMENTS

| | | |
|---|---|---|
| JP | 2002-526146 A | 8/2002 |
| WO | WO 99/36490 A1 | 7/1999 |

OTHER PUBLICATIONS

European Official Action ("Communication pursuant to Article 94(3) EPC") dated May 24, 2017 in counterpart European Application No. 09 702 835.1 (6 pages, in English).

European Official Action ("Communication pursuant to Article 94(3) EPC") dated Dec. 12, 2016 in counterpart European Application No. 09 702 835.1 (5 pages, in English).

International Search Report (PCT/ISA/210) dated Feb. 17, 2009, by the Japanese Patent Office as the International Searching Authority for International Application No. PCT/JP2009/050516.

Extended European Search Report and Opinion dated May 10, 2013 by the European Patent Office in European Patent Application No. 09702835.1.

European Search Report dated Apr. 13, 2016 in the corresponding European Patent Application No. 09702835.1 (5 pages).

* cited by examiner

Partial enlarged view

Partial enlarged view

Partial enlarged view

Partial enlarged view

VALVE BODY, PROCESS FOR PRODUCING THE VALVE BODY, AND MEDICAL INSTRUMENT INCLUDING THE VALVE BODY

This application is a division of U.S. patent application Ser. No. 12/838,017 filed on Jul. 16, 2010, which is a continuation of International Application No. PCT/JP2009/050516 filed on Jan. 16, 2009, and claims priority to Japanese Application No. 2008-009725 filed on Jan. 18, 2008, the entire content of each of which is incorporated herein by reference.

TECHNICAL FIELD

The present invention generally pertains to a valve body, a production process and an instrument embodying the valve body. More specifically, the invention relates to a valve body, having useful application in a medical instrument, a process for producing the valve body, and a medical instrument embodying the valve body.

BACKGROUND DISCUSSION

When an elongated member for medical use such as a catheter, a guide wire, etc. is to be guided into a living body, an introducer is oftentimes used.

The introducer includes a cylindrical hub (joint part), a valve body (check valve) disposed in one end portion of the hub, and a tube connected to the other end portion of the hub. An example of a valve body used in the introducer in this manner is one made of a flexible elastic material such as silicone rubber, as described in Japanese Patent Publication No. Hei 2-949.

The valve body is formed with an opening/closing (opening and/or closing) port (e.g., slit or minute hole) which opens or closes as the elongated member is inserted or pulled out. In addition, for reducing the sliding resistance (frictional resistance) on the elongated member when the elongated member is inserted, the valve body should have lubricity on its surface, particularly at the opening/closing port. To meet this requirement, a lubricating liquid such as a silicone oil is applied to the vicinity of the opening/closing port so as to reduce the sliding resistance of the valve body on the elongated member.

When the insertion and pulling-out of the elongated member through the opening/closing port is repeated, however, the lubricating liquid applied in the vicinity of the opening/closing port gradually becomes leaner. Eventually, the lubricating liquid runs out, leading to an increase in the sliding resistance of the elongated member. In the introducer having such a valve body, therefore, the presence of the lubricating liquid influences the sliding properties of the elongated member. Accordingly, the introducer may suffer a problem in that the operability of the elongated member is reduced during use.

In addition, the introducer as a medical instrument may sometimes be subjected to a sterilizing treatment by irradiation with radiant rays. However, the flexible elastic material such as silicone rubber undergoes alteration or deterioration when exposed to radiant rays. The alteration or deterioration is due to the process in which molecular chains in the silicone rubber are cut by the radiant rays and oxygen in the atmospheric air is bonded to the cut ends of the molecular chains. In this manner, the properties of the silicone rubber are changed, whereby the valve body's function is damaged.

For this reason, the conventional valve bodies have a problem that it is difficult to sufficiently sterilize them by use of radiations.

SUMMARY

The valve body disclosed here exhibits characteristics such that the sliding resistance of the valve body is less liable to increase even upon increased sliding operation (increased usage). Also, the valve body possesses excellent radiation resistance and liquid-tightness performance.

The valve body disclosed here includes an opening/closing part which opens upon inserting a member into the opening/closing part and which closes upon withdrawing the member from the opening/closing part. At least the opening/closing part of the valve body has a main body part comprised of a silicone rubber, and a surface layer is provided on a surface of at least the main body part. The surface layer is comprised of silicon oxide.

Preferably, the surface layer has an average thickness of 10 nm to 100 µm.

The surface layer is also preferably composed of an aggregate of silicon oxide.

Further, the surface layer is preferably composed of an aggregate of particles of silicon oxide.

The surface layer can include plural surface layers preferably in the form of a plurality of spaced apart or discrete dots dispersed on a surface of the main body part.

Each of the dot-formed surface layers preferably projects from the surface of the main body part.

The projection height of the projected surface layers is preferably 500 nm to 50 µm.

The plurality of dot-formed surface layers can be arranged in a density of 300 to 3000 pieces/mm$^2$.

The surface layer can also entirely cover a surface of the main body part.

In addition, the valve body preferably further includes, between the main body part and the surface layer, an intermediate layer composed of a material intermediate between a material constituting the main body part and a material constituting the surface layer.

The content of an organic component in the intermediate layer gradually decreases from the main body part side toward the surface layer side.

Further, each of the surface layer and the intermediate layer is formed through modification of the whole part or a part of the silicone rubber into silicon oxide by irradiation with a laser beam. The opening/closing part is preferably composed of at least one slit.

In addition, the valve body can be columnar or plate-like in overall shape.

Examples of the member adapted to be inserted in the valve body include a sheath, a dilator, a catheter, a guide wire or a needle.

Another aspect disclosed here involves a process for producing a valve body comprising an opening/closing part which opens upon inserting a member into the opening/closing part and which closes upon withdrawing the member from the opening/closing part. The process comprises forming a surface layer comprised of silicon oxide at least in a region that includes the opening/closing part, and the surface layer comprised of silicon oxide is formed on a surface of a base material having the opening/closing part, the base material on which is formed the surface layer comprised of silicon oxide being a silicone rubber.

In addition, the surface layer of the base material is preferably formed by irradiating at least a region of a surface of the opening/closing part with a laser beam so that the silicone rubber in the vicinity of the surface in the region is modified into silicon oxide and raised.

The laser beam has a wavelength of not more than 200 nm.

The irradiation with the laser beam is carried out through a photomask having a window part of a predetermined shape, whereby modification from the silicone rubber into silicon oxide is effected in a region, having a shape corresponding to the predetermined shape, of the surface of the opening/closing part.

The photomask is preferably composed of a mesh-shaped member or a punching metal.

In addition, the surface layer is preferably formed by forming a layer of silicon oxide at least in a region of a surface of the opening/closing part.

The surface layer can be formed by forming a silicon layer at least in a region on a surface of the opening/closing part, and thereafter subjecting the silicon layer to an oxidizing treatment so as to modify silicon into silicon oxide.

Another aspect disclosed here involves a medical instrument comprising a tubular medical instrument main body through which extends a lumen which is open at opposite ends, and a valve body positioned in the lumen of the tubular medical instrument main body. The valve body comprises an opening/closing part which opens when an elongated member is slidably inserted into the opening/closing part and which closes when the elongated member is slidably withdrawn from the opening/closing part. At least the opening/closing part of the valve body has a main body part made of a silicone rubber, and the main body possesses a surface on which is provided a surface layer that contacts the elongated member when the elongated member is slidably inserted into the opening/closing part. The surface layer which contacts the elongated member when the elongated member is slidably inserted into the opening/closing part is a material different from the main body part. The material forming the surface layer includes silicon oxide.

The medical instrument can be an introducer or a Y-connector.

BRIEF DESCRIPTION OF THE DRAWING FIGURES

Figure 1:
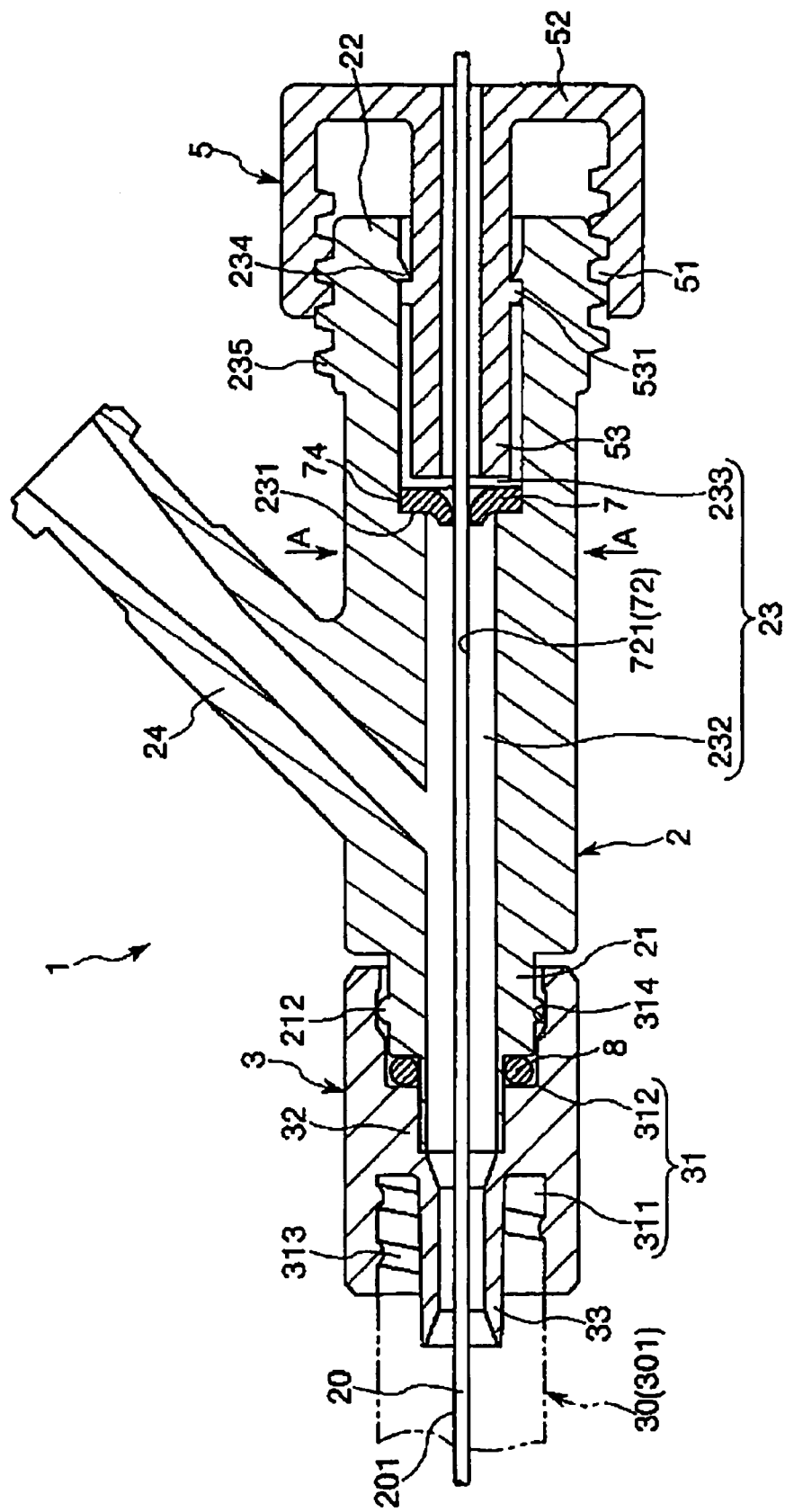
FIG. 1 is a longitudinal cross-sectional view of a medical instrument, in the form of a connector, embodying the valve body disclosed here.
Figure 3A:
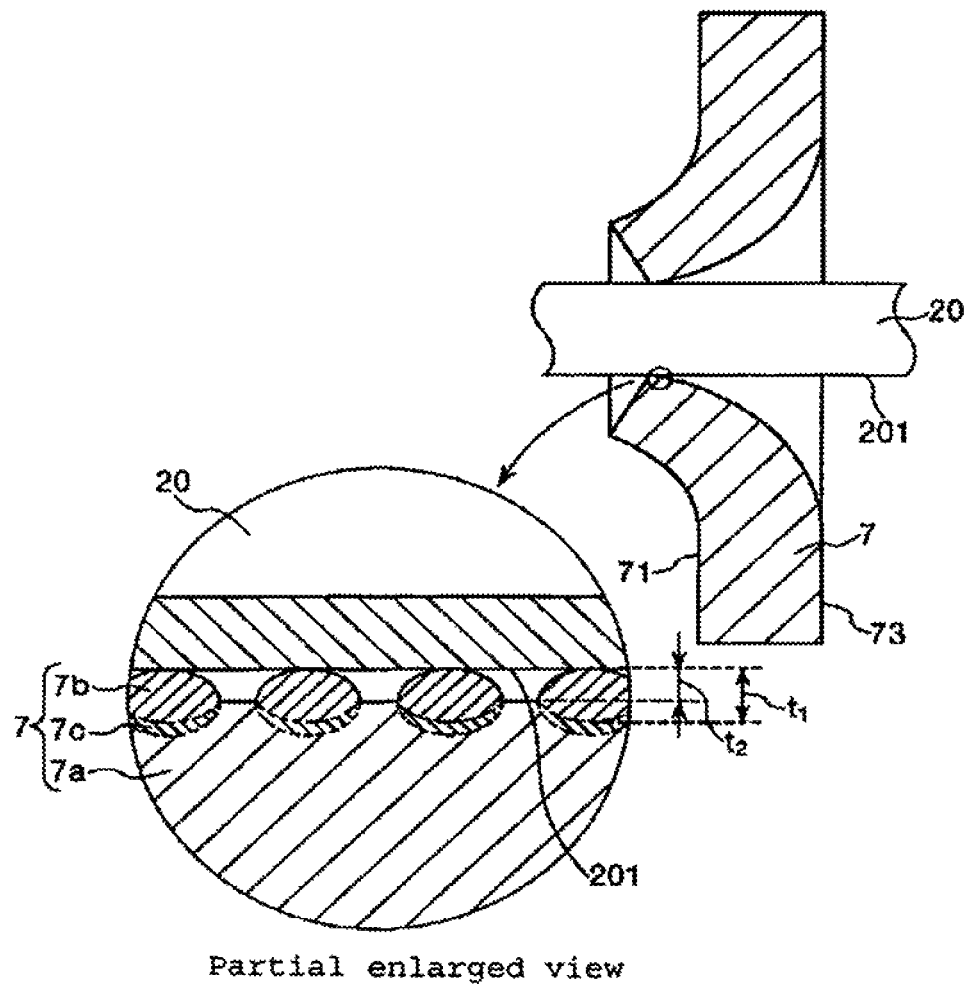
Figure 3B:
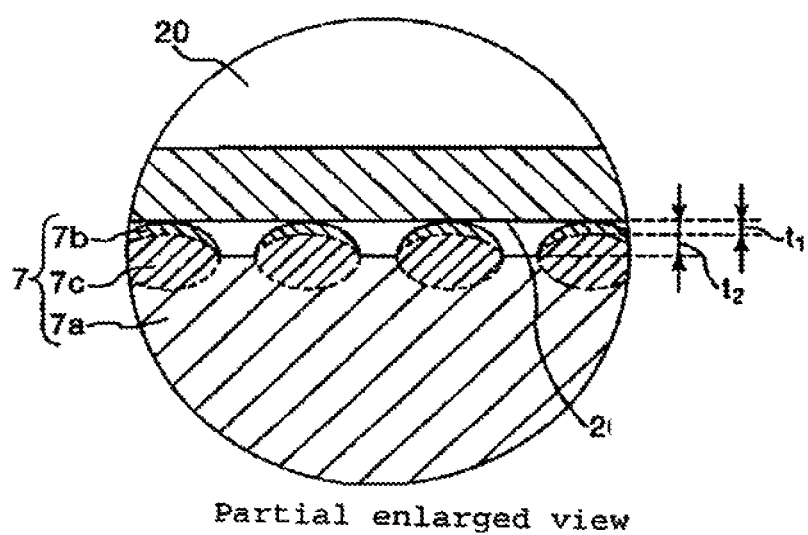

FIGS. 3(a) and 3(b) are enlarged views of a portion of the valve body shown in FIG. 1, specifically the circled portion of the valve body noted in FIG. 3(a).

Figure 4A:
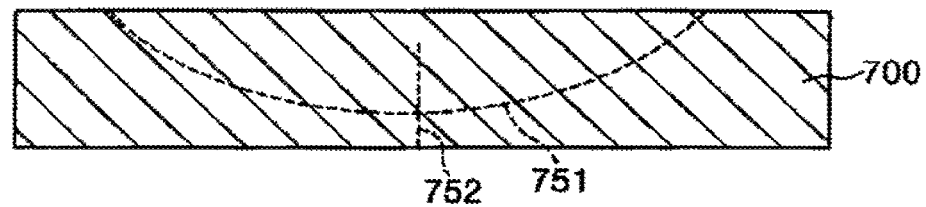
Figure 4B:
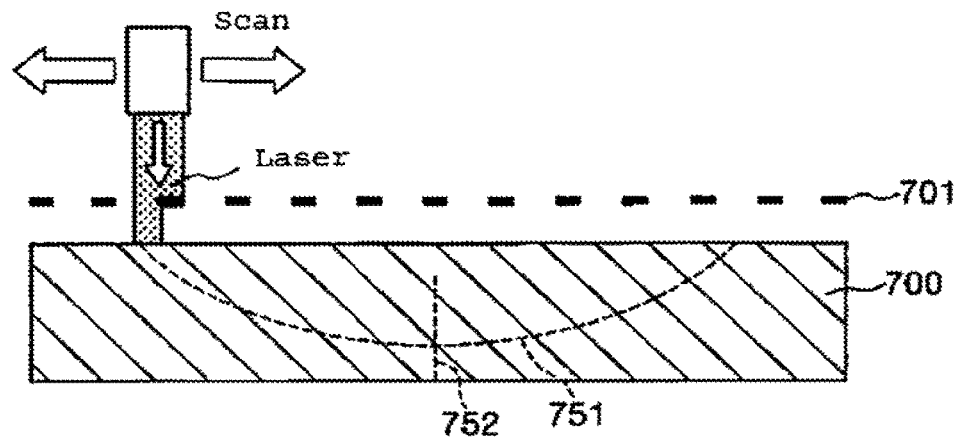
Figure 4C:
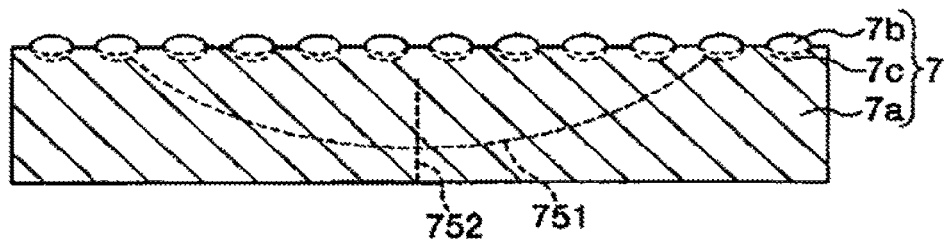

FIGS. 4(a)-4(c) are schematic illustrations, viewed in cross-section, of a process for producing the valve body shown in FIGS. 3(a) and 3(b).

Figure 5:
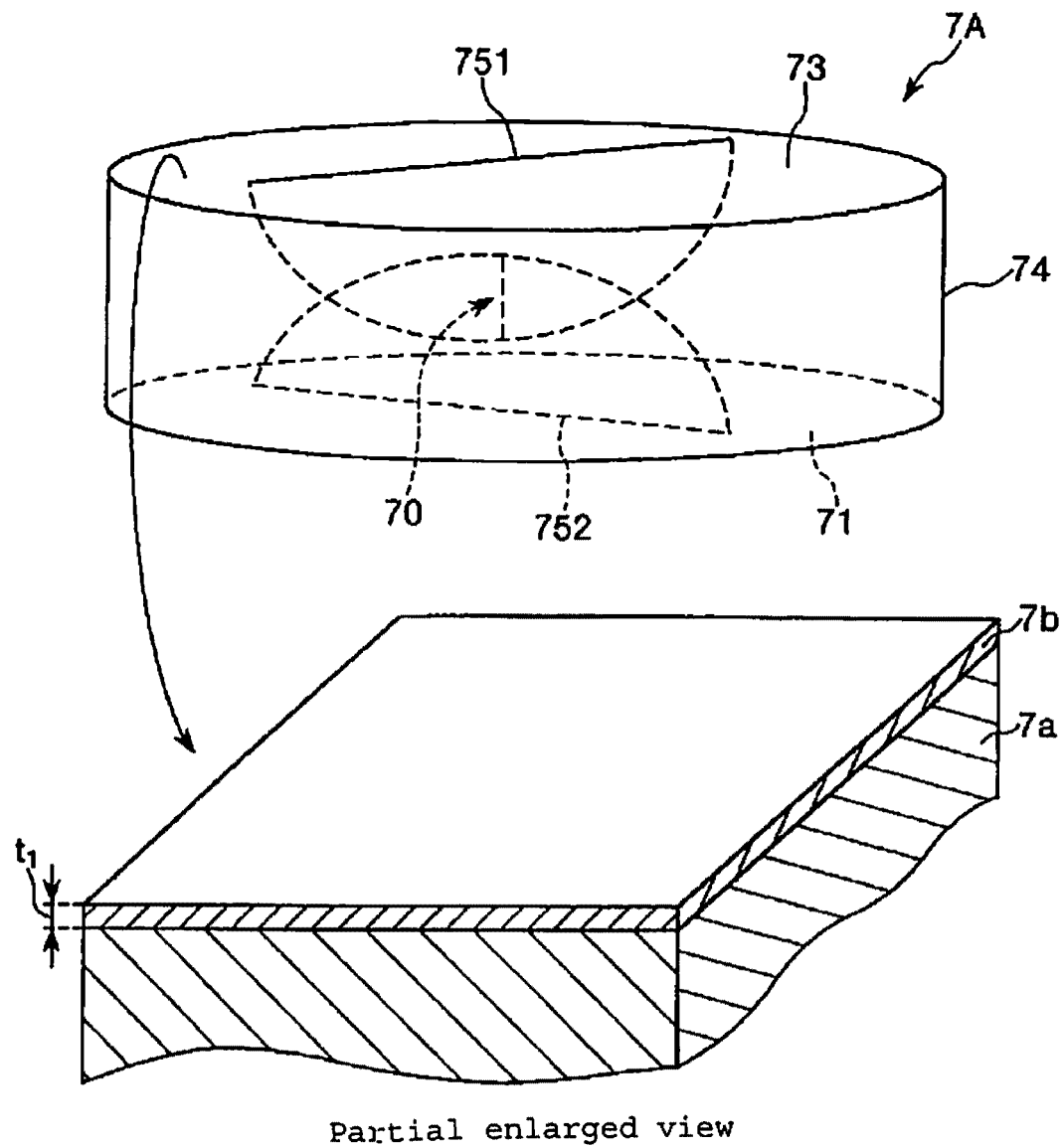

FIG. 5 is a perspective view of a second embodiment of the valve body disclosed here, including an enlarged illustration of a portion of the valve body.

Figure 6A:
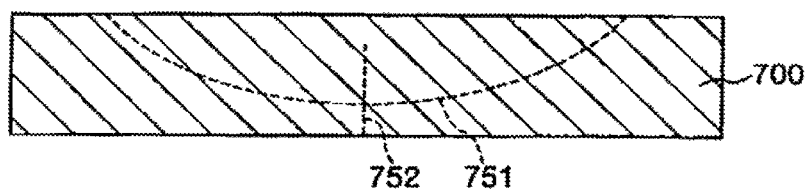
Figure 6B:
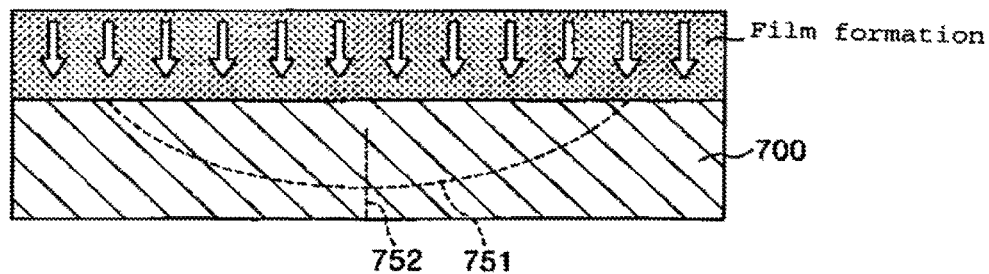
Figure 6C:
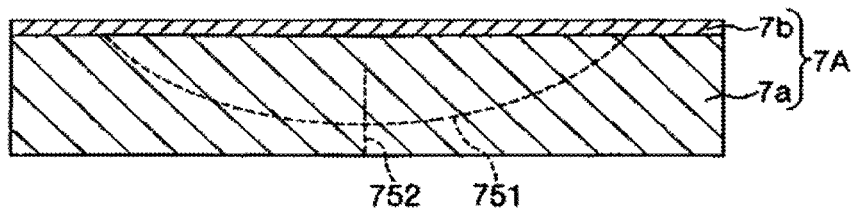

FIGS. 6(a)-6(c) are schematic illustrations, viewed in cross-section, of a process for producing the valve body shown in FIG. 5.

Figure 7:
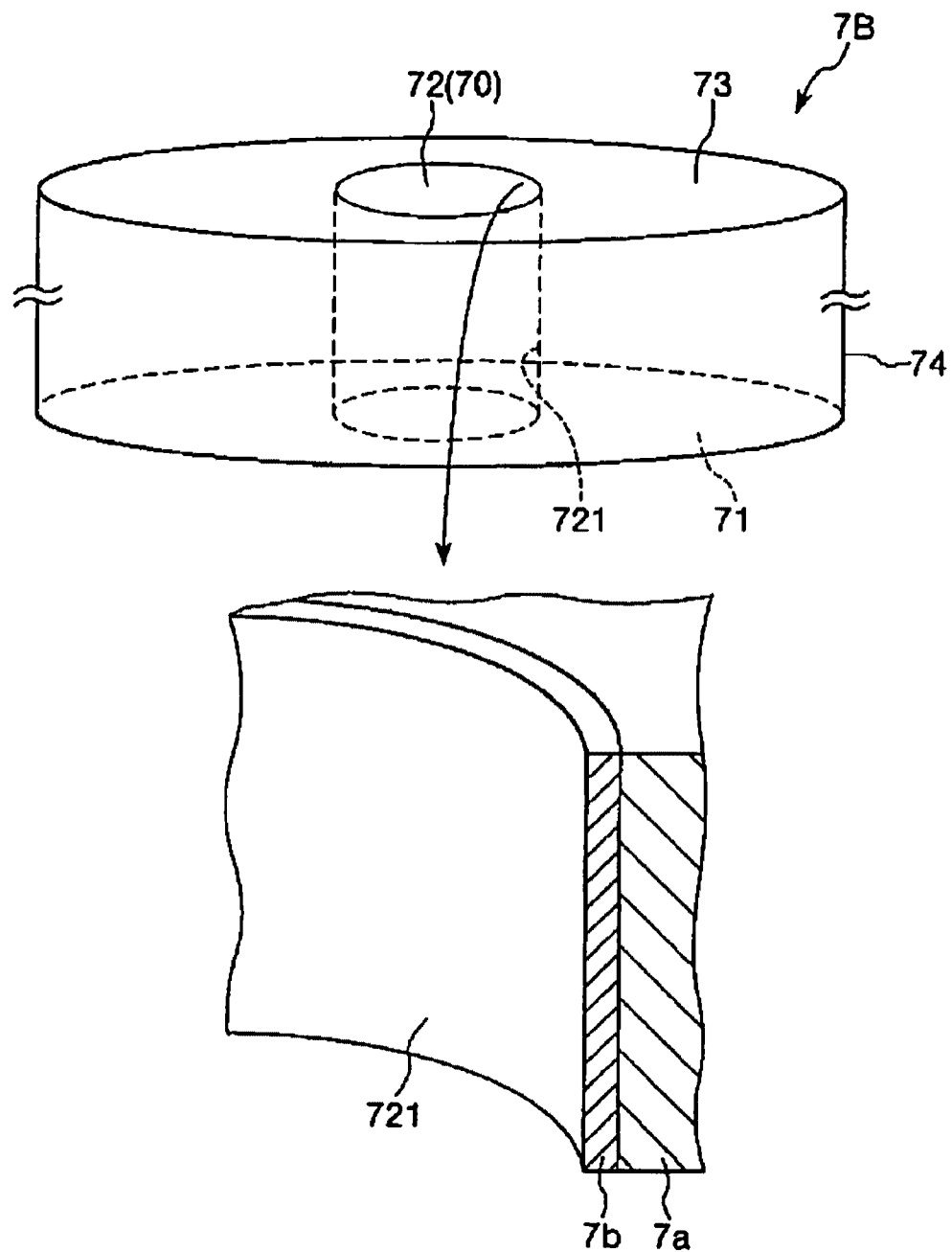

FIG. 7 is a perspective view of a third embodiment of the valve body disclosed here, including an enlarged illustration of the noted circled portion of the valve body.

Figure 8:
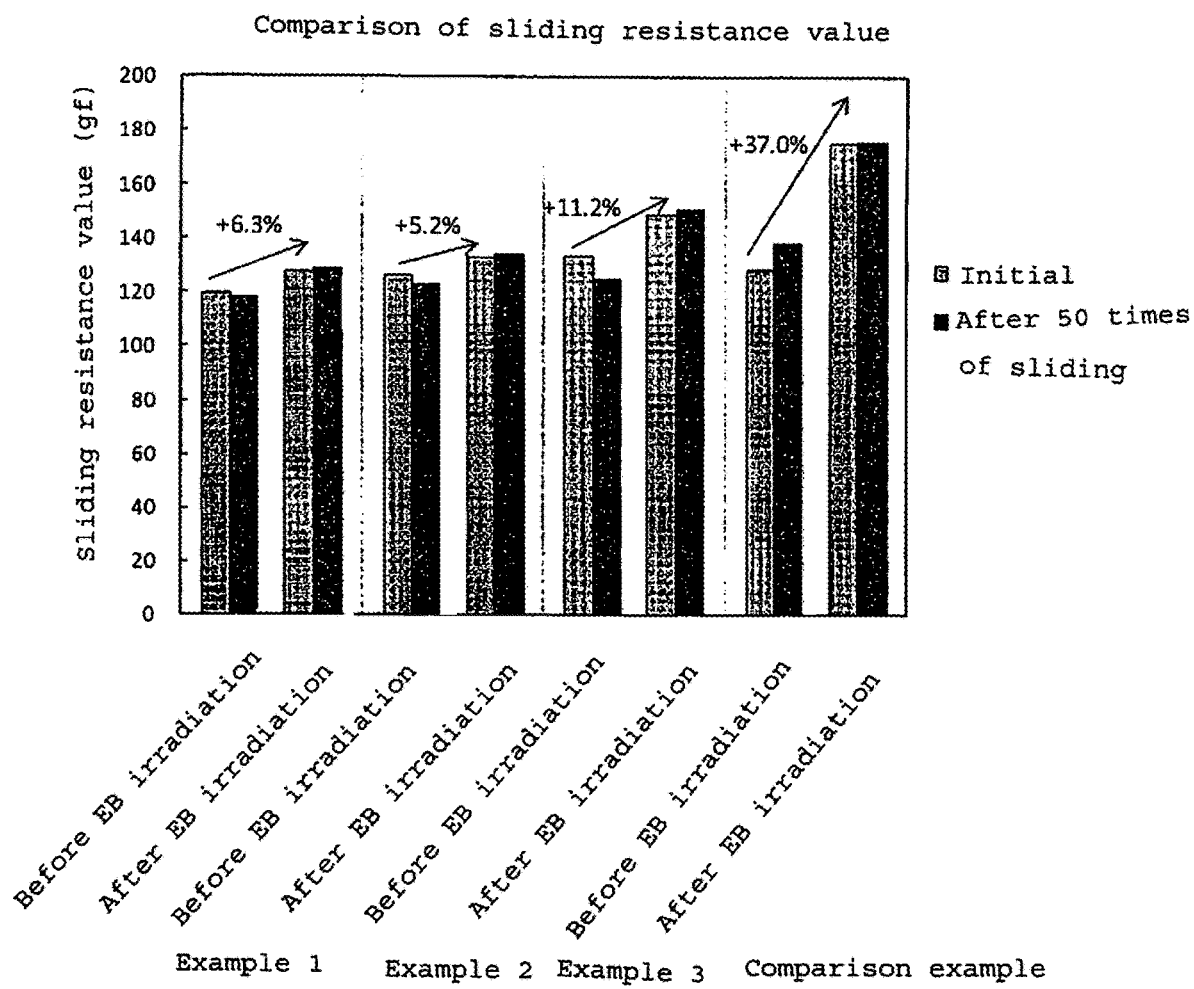

FIG. 8 is a graph comparing evaluation results of examples of connectors disclosed here and comparative examples of connectors.

DETAILED DESCRIPTION

A valve body, a process for producing a valve body, and a medical instrument embodying the valve body are described in more detail below.

Figure 2:
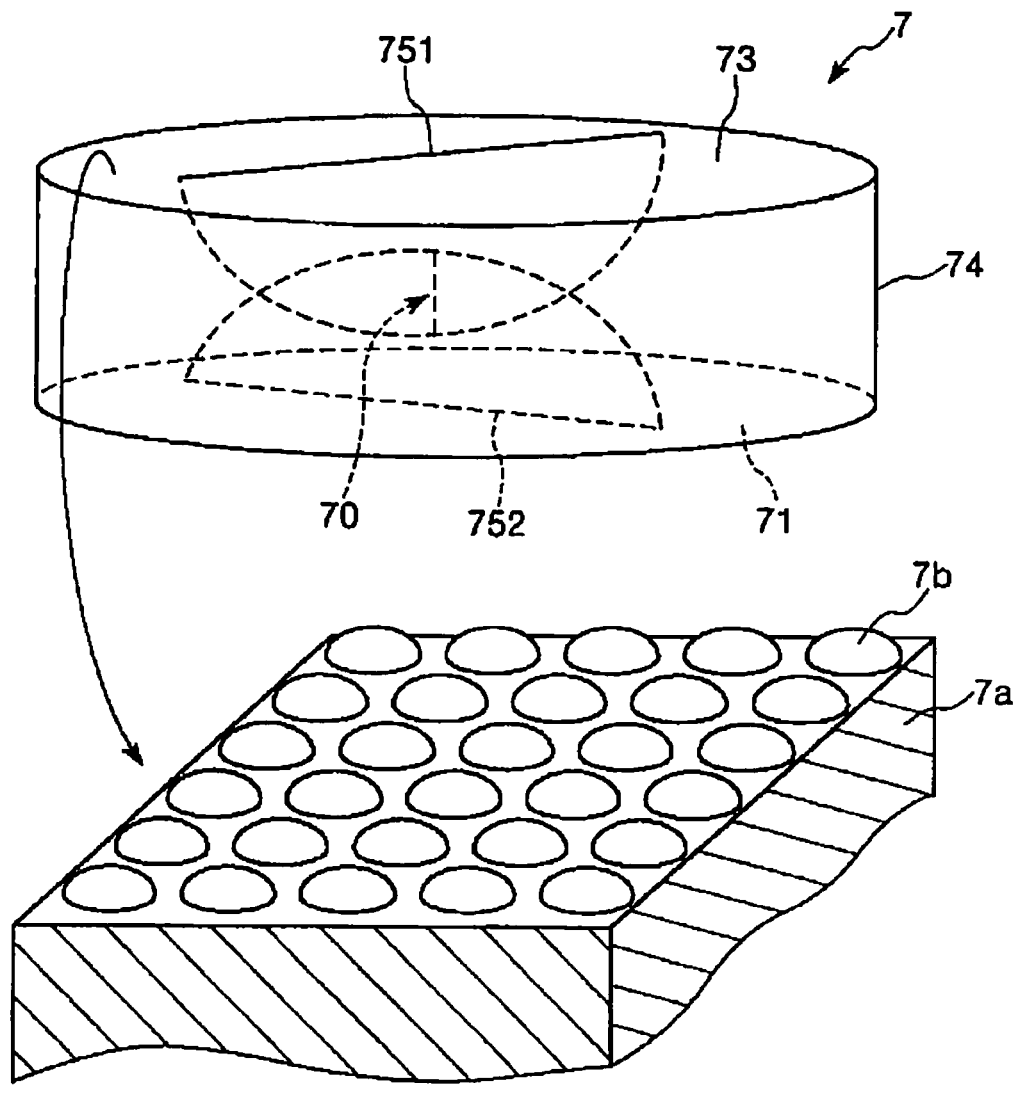
FIG. 2 is a perspective view of a first embodiment of the valve body embodied in the medical instrument shown in FIG. 1.

One disclosed embodiment of the valve body, medical instrument and manufacturing process is illustrated in FIGS. 1-3. For convenience of description, the right side in FIGS. 1 and 3 is referred to as the proximal, and the left side is referred to as the distal.

FIG. 1 illustrates an example of a medical instrument 11 with which the valve body disclosed here has useful application. The medical instrument is a connector, for example a connector used in connection with a hub 301 of a catheter 30. The connector 1, in the state of being connected to the hub 301, is configured to, for example, allow introduction of an elongated member (in this embodiment, a guide wire 20) into the catheter 30. The guide wire 20 is composed of, for example, a metallic material such as stainless steel.

The medical instrument 1 includes a tubular-shaped medical instrument main body 2, which in the illustrated embodiment is a connector main body 2, a lock member or lock adaptor 3 turnably supported on a distal portion 21 of the connector main body 2, a cap body (cap) 5 turnably supported on a proximal portion 22 of the connector main body 2, and a valve body 7 disposed in the connector main body 2.

The connector main body 2 includes a lumen (hollow part) 23 completely penetrating or passing through the connector main body 2 in the longitudinal direction so that opposite ends of the connector main body are open. The lumen 23 is configured to include a stepped part 231 where the inside diameter varies (increases) abruptly. The lumen 23 is divided, with the stepped part 231 as a boundary, into a reduced diameter part 232 on the distal side and an enlarged diameter part 233 on the proximal side.

In the enlarged diameter part 233, the valve body 7 is accommodated (disposed) with its distal end face 71 in abutment with the stepped part 231. This fixes the position of the valve body 7 relative to the connector main body 2. That is, the valve body 7 is positioned. In addition, the enlarged diameter part 233 is provided, on the proximal side, with a circumferentially extending inwardly projecting part 234. The projecting part 234 helps prevent the cap body 5 from slipping off the main body 2 toward the proximal side.

The proximal portion 22 of the connector main body 2 is provided, at the outer peripheral portion, with a male screw part 235. The male screw part or threaded part 235 meshes with a female screw part 51 of the cap body 5 as described later.

The distal portion 21 of the connector main body 2 is provided, at its outer peripheral portion, with a circumferentially extending outwardly projecting part 212. The projecting part 212 helps prevent the lock member 3 from slipping off the main body 2 toward the distal side, and rotatably supports the lock member 3.

The connector main body 2 has a branch part 24 branching from an intermediate portion of the main body. The branch part 24 is tubular in shape, and communicates with the reduced diameter part 232 (lumen part 23) of the connector main body 2. To the branch part 24, for example, a prefilled syringe (not shown) filled with a liquid such as a drug, a radiopaque material, etc. is connected. In the example where the prefilled syringe is connected, the liquid can be supplied from the prefilled syringe into the catheter 30 through the branch part 24 (connector 1).

The branch part 24 is inclined toward the proximal side relative to the connector main body 2. That is, the centerline of the branch part 24 is oblique relative to the centerline of the main body 2. This helps ensure that the liquid flows smoothly in the distal direction from the branch part 24 through the connector main body 2 and, hence, the liquid can be relatively assuredly supplied into the catheter 30.

The lock member 3 is a cylindrical member which has a lumen 31. The lock member 3 is provided, near its middle portion, with a reduced diameter part 32 where its inside diameter is reduced.

In the illustrated embodiment, the lumen 31 is divided, with the reduced diameter part 32 as a boundary, into a distal-side lumen part 311 on the distal side and a proximal-side lumen part 312 on the proximal side.

The inner peripheral surface of the distal-side lumen part 311 possesses a female screw part 313. The female screw part 313 is configured to mesh with a male screw part on the hub 301 of the catheter 30. The meshing engagement between these screw parts (threaded parts) securely connects the lock member 3 (connector 1) and the catheter 30 to each other.

In addition, the reduced diameter part 32 is provided with a tubular part 33 projecting in a tubular shape in the distal direction from the reduced diameter part 32. The tubular part 33 projects distally beyond the portion of the lock member 3 positioned radially outwardly of the tubular part 33. This tubular part 33 is connected in a liquid-tight manner to the hub 301 of the catheter 30 when the female screw part 313 of the lock member 3 and the male screw part of the hub 301 mesh with each other. This helps ensure that, when a liquid is supplied into the catheter 30 through the connector 1, leakage of the liquid is relatively reliably prevented.

The distal portion 21 of the connector main body 2 is positioned in the proximal-side lumen part 312. The inner peripheral surface of the proximal-side lumen part 312 is formed with a recess 314 into which the projected part 212 of the distal portion 21 of the connector main body 2 is fitted. The recess 314 is ring-shaped or annular, extending continuously in the circumferential direction of the inner peripheral surface of the proximal-side lumen part 312. With the projecting part 212 of the connector main body 2 fitted in the recess 314, the lock member 3 can be turned or rotated relative to the connector main body 2 (distal portion 21). As a result, the lock member 3 can be connected, in a meshed state, to the hub 301 of the catheter 30.

A ring-shaped member (seal member) 8 having an annular shape is disposed in the proximal-side lumen part 312. The ring-shaped member 8 is formed of an elastic material. In the connector 1, the connector main body 2 and the lock member 3 are connected in a liquid-tight manner to each other through the ring-shaped member 8. This helps ensure that, when a liquid is supplied into the catheter 30 through the connector 1, the liquid can be prevented from leaking through the vicinity of the joint part between the connector main body 2 and the lock member 3.

The cap body 5 has a bottomed cylindrical shape. The inner peripheral surface of the cap body 5 is formed with the female screw part 51 that meshes with a male screw part 235 of the connector main body 2. The meshing engagement of these screw parts or threaded parts allows the cap body 5 to be moved along the longitudinal direction of the connector main body 2 while rotating relative to the connector body 2.

In addition, a bottom part 52 of the cap body 5 is provided with a tubular part 53 projecting in a tubular shape along the distal direction. The tubular part 53 is positioned in the enlarged diameter part 233 of the connector main body 2. When the cap body 5 is rotated (for example, rotated clockwise) in this condition (in the condition shown in FIG. 1), the tubular part 53 approaches the valve body 7 from the distal side, eventually pressing the valve body 7, namely deforming the valve body 7. The outer peripheral portion of the tubular part 53 includes a circumferentially extending projecting part 531, on the distal side relative to the projecting part 234 of the connector main body 2. The projecting part 531 is able to abut the projecting part 234 of the connector main body 2 from the distal side of the projecting part 234 to thus restrict movement of the cap body 5 in the proximal direction. This helps prevent the cap body 5 from slipping off from the connector main body 2.

The materials constituting the connector main body 2, the lock member 3 and the cap body 5 are not particularly limited. Examples of materials which can be used for these components include various resins such as polyvinyl chloride, polyethylene, polypropylene, cyclic polyolefins, polystyrene, poly(4-methylpentene-1), polycarbonate, acrylic resin, acrylonitrile-butadiene-styrene copolymer, polyesters such as polyethylene terephthalate, polyethylene naphthalate, etc., butadiene-styrene copolymer, and polyamides (e.g., nylon 6, nylon 6,6, nylon 6,10, nylon 12).

The material constituting the ring-shaped member 8 is also not particularly limited. Examples of material which can be used here include elastic materials, for example, natural rubber, various synthetic rubbers such as isoprene rubber, silicone rubber, urethane rubber, styrene-butadiene rubber, fluororubber, acrylic rubber, etc., and various thermoplastic elastomers based on polyamide, polyester, or the like.

As shown in FIG. 2, the valve body 7 is a circular disc-shaped member possessing a relatively short cylindrical overall shape (outside shape). A major part of the valve body 7 is formed of a silicone rubber. The valve body 7 includes a distal end face 71 facing in the distal direction when mounted in the main body 2 and a proximal end face 73 facing in the proximal direction when mounted in the main body 2.

The valve body 7 shown in FIG. 2 has an opening/closing part 70 which, when an elongated member such as a guide wire 20 is inserted, opens or closes while allowing the guide wire 20 to slide. The opening/closing part 70 of the valve body 7 is composed of a first slit 751 and a second slit 752 which open and close as the guide wire 20 is inserted and pulled out.

The first slit 751 extends from the inside or interior of the valve body 7 toward one of the end faces (proximal end face) 73 of the valve body so that the first slit 751 only intersects one of the end surfaces 73 of the valve body 7. Thus, the first slit 751 only opens to the proximal end face 73 of the valve body. In addition, the first slit 751 is in the shape of a straight line in plan view. As a result, the first slit 751 possesses a relatively simple shape (configuration) and so the first slit 751 (opening/closing part 70) can be opened and closed relatively easily and reliably.

The first slit 751 is in the shape of a circular arc in side view. The first slit 751 is positioned so that the vertex of the circular arc of the first slit 751 touches or intersects the second slit 752. This is beneficial from the standpoint that the guide wire 20 can be smoothly moved from the first slit 751 into the second slit 752.

The second slit 752 extends from the inside or interior of the valve body 7 toward the other end face (distal end face) 71 of the valve body so that the second slit 752 only intersects one of the end surfaces 71 of the valve body 7. Thus, the second slit 752 only opens to the distal end face 71 of the valve body. Like the first slit 751, the second slit 752 is in the shape of a straight line in plan view. Consequently, the second slit 752 is relatively simple in shape (configuration) and so the second slit 52 (opening/closing part 70) can be opened and closed relatively easily and assuredly.

Also, like the first slit 751, the second slit 752 is in the shape of a circular arc in side view. This provides a benefit similar to that discussed above. Further, since both faces (the distal end face and the proximal end face) are the same in shape, when the valve body 7 is assembled into the connector 1, the valve body 7 can be assembled without any possibility of making a mistake in recognizing the front side and the back side of the valve body 7, so that the efficiency of the assembling work can be enhanced.

In addition, the first slit 751 and the second slit 752 as described above and illustrated in FIG. 2 partially intersect each other in the inside or interior of the valve body 7. In the illustrated configuration, the first slit 751 and the second slit 752 intersect each other at right angles. Namely, the angle of intersection of the first slit 751 and the second slit 752 is 90°. However, it is to be understood that the intersection angle is not limited to 90°.

In the connector 1 having the valve body 7 as above, when the cap body 5 is rotated, the tubular part 53 presses the valve body 7, in the thickness-wise direction, from the proximal side (i.e., from the right side in FIG. 2) of the valve body. By virtue of this pressing, the valve body 7 might be elastically deformed to be enlarged in outside diameter. However, the outer peripheral surface 74 of the valve body 7 is restricted or constrained by the inner peripheral surface of the enlarged diameter part 233 and so the valve body 7 cannot be enlarged in outside diameter. Consequently, the inside diameter of the valve body 7 is reduced (changed). This ensures that the guide wire 20 inserted in the opening/closing part 70 is pressed (compressed) by the opening/closing part 70 in the directions of the arrows A in FIG. 1, so that the guide wire 20 is securely fastened or held.

In the condition where the guide wire 20 is thus fastened (the condition will hereinafter be referred to as "the fastened condition"), for example, the possibility of liquid flowing-out (leaking-out) from the inside of the connector main body 2 through the opening/closing part 70 of the valve body 7 is reliably inhibited or prevented.

In the connector 1 having the valve body 7 as described above and illustrated in the drawing figures, when the guide wire 20 is inserted in the opening/closing part 70 of the valve body 7 as shown in FIGS. 1 and 3, the silicone rubber in the vicinity of the opening/closing part 70 is curved in the manner of being pressed by the inserted guide wire 20. Where an operation of moving the guide wire 20 in its longitudinal direction is conducted under this condition, the proximal end face 73 of the valve body 7 functions as a sliding part which slides on the outer peripheral surface (outer peripheral part) 201 of the guide wire 20. Since the silicone rubber is elastic, a repelling force is generated in the curved portion of the valve body 7. Therefore, even when the guide wire 20 is operated, the liquid-tightness between the proximal end face 73 of the valve body 7 and the outer peripheral surface 201 of the guide wire 20 is maintained.

Accordingly, the liquid in the connector main body 2 is securely inhibited or prevented from leaking out through the opening/closing part 70.

In the illustrated and described embodiment, the opening/closing part 70 of the valve body is composed of the two slits. However, the valve body is not limited to this configuration. For example, the opening/closing part 70 may be composed of one slit or may be composed of three or more slits.

In addition, while each of the slits is in the shape of a straight line in plan view, this configuration is not limitative. For example, the shape of each slit may be the shape of the letter Y, katakana character "ト," letter V, letter U, or the like.

As shown in FIG. 3, the valve body 7 includes a main body part 7a composed of silicone rubber, and a surface layer 7b provided on an upper surface (proximal end surface 73) of the main body part 7a.

Of these components, the main body part 7a is constituted or composed of a silicone rubber.

The silicone rubber is a rubber material in which a main chain of molecular bonds is composed of silicon-oxygen bonds (siloxane linkages). The silicone rubber is an elastic material excellent in restoration properties in response to compression and/or deformation in a wide temperature range. Therefore, when the guide wire 20 is inserted in the opening/closing part 70 of the main body part 7a, the main body part 7a composed of the silicone rubber shows excellent follow-up properties to the shape of the outer periphery of the guide wire 20. That is, the silicone rubber conforms quite well to the shape of the guide wire 20. This helps ensure that the liquid-tightness between the opening/closing part 70 and the outer peripheral surface 201 of the guide wire 20 is maintained to a relatively high degree, so that flowing-out of the liquid present in the connector main body 2 can be relatively reliably inhibited or prevented.

On the other hand, the surface layer 7b is constituted or composed of a material different from the material forming the main body part 7a. More specifically, the surface layer 7a is constituted or composed of silicon oxide.

With this construction, when the guide wire 20 is inserted in the opening/closing part 70, the main body part 7a and the surface layer 7b in the vicinity of the opening/closing part 70 are curved toward the distal side while being pressed by the inserted guide wire 20 as shown in FIG. 3. Consequently, as shown in FIG. 3, the surface layer 7b of the valve body 7 mainly slides on the outer peripheral surface 201 of the guide wire 20 at the time of insertion of the guide wire. Therefore, the sliding resistance exerted on the guide wire 20 inserted in the opening/closing part 70 arises mainly from a resisting force generated between the surface layer 7b near the opening/closing part 70 and the outer peripheral surface 201 of the guide wire 20.

In the valve body disclosed here, the surface layer 7b is constituted of silicon oxide as above-mentioned, whereby a reduction in the resistance of sliding of the surface layer 7b on the guide wire 20 is achieved. The reason for this is presumed to be due, at least in part, to the silicon oxide constituting the surface layer 7b being relatively low in flexibility and elasticity (lower in flexibility and elasticity than the silicone rubber forming the main body part 7a) and, hence, it is restrained from a behavior in which the surface layer 7b tends to adhere to the guide wire 20 or in which the surface layer 7b tends to be inhibited from sliding relative to the guide wire outer surface. Therefore, with the valve body 7 having the surface layer 7b as just-mentioned, the guide wire 20 can slide on the surface layer 7b in a slipping-type of manner.

As a result, the valve body 7 can realize relatively high operability of the guide wire 20 inserted in the opening/closing part 70, while sufficiently securing liquid-tightness between the valve body 7 and the guide wire 20.

In addition, the surface layer 7b is provided on a surface of the main body part 7a composed of the silicone rubber. Therefore, the influence of the surface layer 7b on the mechanical properties of the valve body 7 is quite slight, and the mechanical properties of the valve body 7 as a whole are determined predominantly by the mechanical properties of the silicone rubber constituting the main body part 7a. In other words, the valve body 7 exhibits relatively excellent sliding properties on the guide wire 20 offered by the surface layer 7b, while retaining the flexibility and elasticity properties exhibited by the silicone rubber.

Furthermore, the valve body 7 shows sufficient sliding properties so as not to hamper the operations of the guide wire 20, without the need for using a lubricating liquid (e.g., silicone oil) which has been necessary in the case of conventional valve bodies. This makes it possible to omit the use of a lubricating liquid. Therefore, it is possible to omit the work of applying a lubricating oil to the valve body 7. In addition, a problem such as the gradual increase in the sliding resistance due to run-out (consumption) of a lubricating liquid attendant on operations of the guide wire 20 can be avoided. Therefore, the operator of the guide wire 20 can operate the guide wire 20 with a relatively fixed force even when the number of times of sliding is increased. Accordingly, the connector 1 having the valve body 7 generally promises excellent operability of the guide wire 20.

Also, by avoiding the use of a lubricating liquid, there is no fear that a lubricating oil is dissolved into the liquid in contact with the valve 7.

Further, silicon oxide is superior to silicone rubbers in durability against radiation. On the other hand, a silicone rubber would suffer cutting of its molecular chain when exposed to radiations. Then, oxygen in the atmospheric air would be bonded to the cut ends, whereby the silicone rubber would be oxidized. The silicone rubber thus oxidized possesses lowered intrinsic properties such as flexibility and elasticity, leading to fissuring or cracking.

On the other hand, in this embodiment, a surface (proximal end face) of the main body part 7a composed of the silicone rubber is covered with the surface layer 7b. Therefore, even if the molecular chains of the silicone rubber constituting the main body part 7a are cut by radiation, a gas barrier effect of the surface layer 7b reduces the chance for the silicone rubber to make contact with oxygen in the air. Consequently, alteration or deterioration of the silicone rubber is restrained, and generation of fissures or cracks can be inhibited or prevented.

The silicon oxide constituting the surface layer 7b is not particularly limited regarding the valence of silicon; in general, however, silicon dioxide is preferably used.

In the surface layer 7b, the crystal structure of silicon oxide is not particularly limited, but may be single-crystalline, polycrystalline or amorphous.

In addition, the surface layer 7b is preferably composed of an aggregate of particles of silicon oxide. This helps ensure that the surface layer 7b is relatively rich in flexibility. Accordingly, shape follow-up properties of the surface layer 7b in relation to the main body part 7a upon curving of the opening/closing part 70 of the valve body 7 will be relatively high. Consequently, the surface layer 7b can be relatively securely prevented from peeling from the main body part 7a.

The diameter of the silicon oxide particles is not particularly limited, but varies depending on the thickness of the surface layer 7b. Preferably, however, the particle diameter is about 1 nm to 10 µm, more preferably about 1 nm to 1 µm.

The surface layer 7b preferably has an average thickness t1 of about 10 nm to 100 µm, more preferably about 50 nm to 50 µm (see FIG. 3). When the average thickness t1 of the surface layer 7b is in this range, liquid-tightness of the valve body 7 is sufficiently secured, yet excellent sliding properties on the guide wire 20 are exhibited. Besides, concern about permeation of oxygen through the surface layer 7b is lowered, and the silicone rubber constituting the main body part 7a can be relatively securely restrained from undergoing alteration or deterioration.

If the average thickness t1 of the surface layer 7b is below the above-mentioned lower limit, the sliding resistance exerted on the guide wire 20 may be raised conspicuously. In addition, permeation of oxygen through the surface layer 7b may occur. On the other hand, if the average thickness t1 of the surface layer 7b exceeds the above-mentioned upper limit, the flexibility and/or elasticity of the valve body 7 may be undesirably lowered. Specifically, since the surface layer 7b is too thick, the opening/closing part 70 may become difficult to curve, the guide wire 20 may become difficult to insert, and the liquid-tightness of the valve body 7 may be lowered.

In the illustrated embodiment, the surface layer 7b is composed of a plurality of surface layers 7b dispersed in the form of dots as shown in FIGS. 2 and 3. Each of the surface layers 7b projects (in the form of a projectingly deformed part or a protruding part) from the surface of the main body part 7a as shown in FIG. 3. Therefore, when the guide wire 20 is inserted in the opening/closing part 70, the surface layers 7b preferentially make contact with the outer peripheral surface 201 of the guide wire 20. As a result, due to the presence of the surface layers 7b, the surface area of the valve body 7 in sliding contact with the guide wire 20 is reduced, whereby the sliding resistance exerted on the guide wire 20 is also reduced. In addition, since the plurality of the surface layers 7b are formed in a partial manner (i.e., in this embodiment, the surface layers 7b exist on a portion of the surface of the valve body, but not the entire surface of the valve body), a reduction in the sliding resistance can be achieved without considerably lowering the mechanical properties such as flexibility and elasticity of the silicone rubber. Consequently, the valve body 7 can simultaneously show, at a high extent, both excellent sliding properties on the guide wire 20 and relatively high liquid-tightness.

In addition, preferably, each of the surface layers 7b is hemispherical (dome-like) in shape, as shown in FIG. 2. This helps ensure that the area of contact of the surface layers 7b with the guide wire 20 is particularly reduced, preferably minimized. As a result, the sliding resistance exerted on the guide wire 20 can be particularly reduced.

Each of the surface layers 7b shown in FIG. 2 is so provided that it is partly embedded in the main body part 7a as also shown in FIG. 3. Such surface layers 7b are thus fixed in such a manner that they are held by the main body part 7a and are relatively securely prevented from peeling off.

The projection height t2 by which the surface layers 7b project from the surface of the main body part 7a is preferably about 500 nm to 50 µm, more preferably about 800 nm to 2 µm (see FIG. 3). When the projection height t2 of the surface layer 7b is within the just-mentioned range, the sliding resistance of the valve body 7 on the guide wire 20 can be lowered relatively assuredly. The size of gaps formed between the main body part 7a and the guide wire 20 is suppressed or reduced to such a level that a liquid cannot pass through the gap. Accordingly, the liquid-tightness at the valve body 7 can be relatively securely prevented from being lowered.

In addition, in the illustrated embodiment shown in FIG. 2, the plurality of surface layers 7b dispersed in the form of dots are distributed evenly and regularly.

The plurality of surface layers 7b provided as above are preferably formed in a formation density of about 300 to 3000 pieces/mm$^2$, more preferably about 1000 to 1500 pieces/mm$^2$. When the formation density is within the just-mentioned range, both the effect of the surface layers 7b on lowering the sliding resistance on the guide wire 20 and the effect of the main body part 7a on the following-up of the shape of the opening/closing part 70 to the outer peripheral surface 201 of the guide wire 20 can be simultaneously realized to an extremely high extent. In addition, the main body part 7a is sufficiently covered with the surface layers 7b so that radiation resistance of the main body part 7a can be enhanced sufficiently.

If the formation density is less than the above-mentioned lower limit, the formation density of the surface layers 7b is too low to sufficiently lower the sliding resistance on the guide wire 20. Also, the area of exposure of the main body part 7a is so large that the radiation resistance of the main body part 7a may be extremely lowered. On the other hand, if the formation density exceeds the above-mentioned upper limit, the opening/closing part 70 is markedly lowered in flexibility and/or elasticity, so that the liquid-tightness of the valve body 7 may be lowered conspicuously.

In addition, the area of each of the surface layers 7b dispersed in the form of dots is preferably about $10^{-12}$ to $10^{-3}$ mm$^2$, more preferably about $10^{-10}$ to $10^{-4}$ mm$^2$.

Both the formation density and the area of each of the surface layers 7b are so set that the proportion in which the surface layers 7b cover the upper surface of the main body part 7a will be within the following range described below. The just-mentioned proportion of the surface layers 7b is preferably about 10% to 100%, more preferably about 20% to 90%. Consequently, a valve body 7 can be obtained which can simultaneously show, to a relatively high extent, both a low sliding resistance on the guide wire 20 and excellent liquid-tightness as well as radiation resistance.

In addition, the plurality of surface layers 7b may each be formed in any shape (pattern) in plan view other than the above-mentioned dot shape, for example, a linear shape, an irregular shape or the like.

While the plurality of surface layers 7b may be distributed regularly, they may also be distributed irregularly.

Further, the formation density of the plurality of surface layers 7b may be even or uneven, over the whole part of the valve body 7.

The plurality of surface layers 7b dispersed in the shape of dots may be formed not only on the upper surface of the valve body 7 but on the whole surface inclusive of side surfaces and a lower surface of the valve body 7. In this case, a radiation resistance of the valve body 7 as a whole can be enhanced.

In addition, as shown in FIG. 3, an intermediate layer 7c is interposed between each of the surface layers 7b and the main body part 7a. The intermediate layer 7c is composed of a material which is intermediate between the material constituting the main body part 7a and the material constituting the surface layers 7b, specifically a material intermediate between the silicone rubber and the silicon oxide. This helps ensure that the intermediate layer 7c shows relatively high adhesion to both the main body part 7a and the surface layers 7b. Therefore, with the intermediate layer 7c thus provided between the main body part 7a and the surface layers 7b, the adhesion strength of the surface layers 7b to the main body part 7a can be enhanced. As a result, as shown in FIG. 3, even if a high load is exerted on the surface layers 7b due to sliding of the surface layers 7b on the outer peripheral surface 201 of the guide wire 20, the surface layers 7b can be relatively securely prevented from peeling off from the main body part 7a.

Further, the intermediate layer 7c preferably has a graded composition such that its composition varies gradually in the thickness direction. Specifically, it is preferable that the content of an organic component in the intermediate layer 7c gradually decreases from the side of the main body part 7a toward the side of the surface layer 7b. Thus, in the disclosed example in which the main body part is comprised of silicon rubber, the silicon rubber contains carbon, an organic component, and this organic component decreases from the side of the main body part 7a toward the side of the surface layer 7b. Such an intermediate layer 7c shows closeness in composition to both the main body part 7a and the surface layers 7b, so that it exhibits a particularly high adhesion to both the main body part 7a and the surface layers 7b. This facilitates a further enhanced adhesion strength between the surface layers 7b and the main body part 7a.

The ratio between the thicknesses of the surface layer 7b and the intermediate layer 7c is not particularly limited. Specifically, the surface layer 7b may be thicker than the intermediate layer 7c, as shown in FIG. 3(a); or, on the contrary, the intermediate layer 7c may be thicker than the surface layer 7b, as shown in FIG. 3(b).

A process for producing the valve body 7 described above will be described below.

FIGS. 4(a)-4(c) schematically illustrate aspects of a process for producing the valve body shown in FIG. 3. In the following description, the upper side in FIGS. 4(a)-4(c) is referred to as "upper" and the lower side is referred to as "lower".

The process for producing the valve body 7 includes: [1] preparing a base material 700 composed of a silicone rubber; and [2] irradiating the upper surface of the base material 700 with a laser beam. Hereafter, each of these aspects of the process disclosed here will be described in detail.

[1] First, as shown in FIG. 4(a), the base material 700 for producing the valve body 7 is prepared. This base material 700 is composed of a silicone rubber, and has the shape of the main body part 7a. In this disclosed embodiment, the base material 700 is composed entirely of silicone rubber. Also, the base material 700 is a circular disc-shaped plate material provided with a first slit 751 and a second slit 752.

[2] Next, as shown in FIG. 4(b), the upper surface of the base material 700 is irradiated with a laser beam. By virtue of this, the silicone rubber in the region irradiated with the laser beam, organic groups linked as side chains to a siloxane constituting a main chain are removed through light cleavage. As a result, the base material 700 in the region irradiated with the laser beam is modified (vitrified) into silicon oxide, to obtain the main body part 7a of the valve body 7 mentioned above and the surface layers 7b which are provided on the surface of the main body part 7a and are constituted of silicon oxide. The outermost portion of the base material 700 forming the surface layers 7b are, in this disclosed embodiment, composed entirely of silicon oxide.

In this embodiment, as shown in FIG. 4(b), the irradiation with the laser beam is carried out by scanning a laser beam along the upper surface of the base material 700 through a photomask 701 having window parts (beam-transmitting parts) in a mesh-like pattern. This helps ensure that the regions reflecting the shapes of the window parts of the photomask 701 are irradiated with the laser beam. Therefore, a plurality of surface layers 7b in the shape of dots (corresponding to the locations of the window parts) are obtained on the upper surface of the main body part 7a.

In addition, since this modification is attended by cubical expansion, the silicone rubber is raised in hemispherical (dome-like) shapes from the upper surface of the base material 700 simultaneously with the change into silicon oxide. In this case, the quantity of heat applied to the silicone rubber by the laser beam is so distributed as to gradually decrease from the upper surface toward the inside of the base material 700. Therefore, even if substantially full modification into silicon oxide occurs at the uppermost surface of the base material 700, the quantity of heat is insufficient and hence parts not fully modified are generated on the lower side of the uppermost surface. Accordingly, areas where the silicone rubber and silicon oxide are present in a mixed manner are formed between the main body part 7a and the surface layers 7b. Thus, the above-mentioned intermediate layer 7c is formed between the main body part 7a and the surface layer 7b. The intermediate layer 7c represents a transition from the surface layers 7b of silicon oxide and the main body part 7a of silicone rubber.

The wavelength of the laser beam with which to irradiate the base material 700 is preferably not more than 200 nm, more preferably not more than 180 nm, still preferably not more than 160 nm. This helps ensure that the laser beam has sufficiently high energy, whereby the side chains of the silicone rubber are more securely put into light cleavage, and oxygen molecules undergo photolysis, to produce a multiplicity of active oxygen atoms. As a result, the multiplicity of active oxygen atoms act on the silicone rubber, so that the silicone rubber is modified into silicon oxide in a short time and assuredly.

The lower limit of the wavelength of the laser beam is not particularly limited. In consideration of the laser beam generating cost and the damage to the main body part 7a, however, the lower limit of the wavelength is about 100 nm. In addition, when the upper surface of the base material 700 is irradiated with the laser beam, the surface layers 7b are raised and, simultaneously, the surface layers 7b are formed also in regions on the inner side relative to the upper surface of the base material 700. Accordingly, the surface layers 7b are so formed as to be embedded from the upper surface into the inside of the base material 700.

Examples of a laser beam source to be used include fluorine laser (F2 laser), ArF (argon fluoride) excimer laser, etc., among which the fluorine laser is preferably used.

The oscillation mode of the laser beam may be either continuous oscillation or pulsed oscillation. In the case of the pulsed oscillation, the energy density per pulse is preferably about 5 to 60 mJ/cm2. The number of pulses per second is about 5000 to 20000 pulses.

In addition, the atmosphere in which to irradiate with the laser beam is an inert gas atmosphere or a reduced pressure atmosphere.

As the photomask 701, there can be used, for example, reticules which are used in semiconductor production processes. Other than the reticules, there can also be used mesh-shaped members, punching metals, and the like.

As an alternative to the use of the photomask 701, irradiation with a laser beam may be conducted under programmed computer control such as to apply the laser beam only to preset regions.

In the above-mentioned manner, the valve body 7 including the main body part 7a, the intermediate layers 7c and the surface layers 7b as shown in FIG. 4(c) is obtained.

FIG. 5 is a perspective view of a second embodiment of the valve body disclosed here. The following description focuses primarily on the differences from the above-described embodiment. Features in this embodiment that are the same as the first embodiment are identified by common reference numerals and a detailed description of such features is not repeated.

This embodiment is the same as the above-described first embodiment except for a difference in the configuration of the surface layer of the valve body.

The valve body 7A shown in FIG. 5 has a configuration in which a surface layer 7b entirely covers an upper surface (proximal end face 73) of a main body part 7a. In this case, the proportion in which the surface layer 7b covers the upper surface of the main body part 7a is 100%. In this instance, the whole part of the upper surface (proximal end face 73) of the main body part 7a is completely covered with the surface layer 7b, so that the chance of contact between the main body part 7a and oxygen is very small. This makes it possible to obtain a valve body 7 which is particularly excellent in radiation resistance.

The average thickness t1 of the surface layer 7b shown in FIG. 5 is the same as the average thickness of the surface layers 7b in the first embodiment above.

A process for producing the valve body 7A shown in FIG. 5 is as follows. FIGS. 6(a)-6(c) schematically illustrate the process for producing the valve body shown in FIG. 5. In the following description, the upper side in FIG. 6 is referred to as the "upper" and the lower side is referred to as the "lower."

The process for producing the valve body 7A includes: [1A] preparing a base material 700 composed of a silicone rubber; and [2A] forming the surface layer 7b on the upper surface of the base material 700. Hereafter, each of the steps will be described in detail.

[1A] First, as shown in FIG. 6(a), the base material 700 for producing the valve body 7 is prepared.

The surface of the base material 700 on which is formed the surface layer 7b as described later may be preliminarily subjected to a roughening treatment. Examples of the roughening treatment include a method of coating with a roughening treating agent for silicone resin, and a method of roughening the surface to be treated.

[2A] Next, as shown in FIG. 6(b), a film of silicon oxide is formed on the upper surface of the base material 700. By this, a surface layer 7b constituted of silicon oxide as shown in FIG. 6(c) is formed on the upper surface of the main body part 7a.

The method for forming the film of silicon oxide is not particularly limited. Examples of the method which can be used here include chemical vapor deposition methods such as plasma CVD method, thermal CVD method, etc., and physical vapor deposition methods such as vacuum evaporation method, sputtering method, ion plating method, etc.

In addition, a method may be adopted in which a film of silicon is once formed, and the silicon film is subjected to an oxidizing treatment to thereby form the surface layer 7b.

In this case, as the method for forming the silicon film, the same method as the method of forming the silicon oxide film mentioned above can be used.

Besides, examples of the oxidizing treatment method include a method of exposing to ozone or hydrogen peroxide, a method of irradiating with UV rays, and a combination of these methods.

In addition, a film of silicon oxide may be formed through a mask. By this, a silicon oxide film is formed in each of regions in shapes corresponding to the shapes of window parts (through-holes) in the mask, resulting in that the surface layer 7b in a predetermined shape is obtained.

As the mask, there can be used, for example, a mesh-shaped member, a punching metal or the like. By forming the film through such a mask provided with a multiplicity of window parts, for example, a plurality of surface layers dispersed in the shape of dots can be easily formed on the upper surface of the main body part 7a.

In the second embodiment of the valve body and the medical instrument according disclosed here, the same effects as those of the first embodiment above can be obtained.

FIG. 7 is a perspective view showing a third embodiment of the valve body disclosed here. The following description focuses primarily on differences between this third embodiment and embodiments of the valve body described earlier. Features in this embodiment that are the same as the embodiments described above are identified by common reference numerals and a detailed description of such features is not repeated.

This third embodiment is the same as the first embodiment described above except for a difference in the configuration of the valve body.

A valve body 7B shown in FIG. 7 is a circular disc-shaped member possessing a relatively short cylindrical overall shape (outside shape). The central portion of the valve body 7B is provided with a through-hole 72 as an opening/closing part 70 capable of being opened and closed. The through-hole 72 is a hole extending from the distal end face 71 to the proximal end face 73 of the valve body 7B, penetrating or passing completely through the valve body 7. With a guide wire 20 inserted in the through-hole 72, the outer peripheral surface 201 of the guide wire 20 slides on the inner peripheral surface 721 of the through-hole 72, whereby liquid-tightness at the sliding surface is maintained.

The through-hole 72 is circularly shaped in plan-view. The inside diameter of the through-hole 72 in a natural condition (the condition shown in FIG. 7) is set to be approximately equal to or slightly larger than (in the configuration shown in FIG. 7, approximately equal to) the outside diameter of the guide wire 20. This helps ensure that the guide wire 20 can inserted in the valve body 7. Here, "natural condition" means the condition where no external force is applied to the valve body 7.

In addition, as shown in FIG. 7, the valve body 7B includes a main body part 7a composed of silicone rubber, and a surface layer 7b on the inner peripheral surface of the main body 7a. This helps ensure that the inner peripheral surface 721 of the through-hole 72 is a surface composed of silicon oxide.

Here, as mentioned above, the inner peripheral surface 721 of the through-hole 72 slides on the outer peripheral surface 201 of the guide wire 20, and, since the inner peripheral surface 721 is composed of silicon oxide, the guide wire 20 can slide on the inner peripheral surface 721 in a slipping manner. This helps enable the operator of the guide wire 20 to efficiently operate the guide wire 20 without exerting a large force.

The surface layer 7b possessed by the valve body 7B as described above may be a surface layer 7b ranging over the whole part of the inner peripheral surface 721 of the through-hole 72 as shown in FIG. 7. However, the surface layer 7b may also be formed as a plurality of surface layers 7b distributed in the form of dots as in the first embodiment.

The surface layer 7b according to this embodiment may be one produced by either the producing method according to the first embodiment and the producing method according to the second embodiment.

In the third embodiment of the valve body and the medical instrument disclosed here, the same effects as those of the first embodiment above can be obtained.

While the valve body, the process for producing the valve body, and the medical instrument disclosed here have been described above based on the embodiments shown in the drawings, the invention here is not limited to these embodiments. Each of the components of the valve body and the medical instrument can be replaced by one with a different configuration which can exhibit the same function as above-mentioned. Also, components may be added to the construction described above.

In addition, the valve body and the medical instrument disclosed here may involve a combination of two or more configurations (features) according to the above-described embodiments.

While a connector has been shown in each of the above embodiments as an example of the medical instrument disclosed here, the medical instrument of the present invention is not limited to the connector, but may also be an introducer, an indwelling needle or the like.

In addition, while a guide wire has been shown in each of the above embodiments as an example of the elongated member inserted into and pulled out of the valve body, the elongated member is not limited to the guide wire, but may also be a sheath, a dilator, a catheter, a needle, a mouth part (distal projected part) projecting at a distal portion of a syringe outer cylinder, or the like.

The process for producing a valve as described above may include additional steps beyond those described above.

EXAMPLES

Now, specific examples implementing the disclosure here are described below.

1. Production of Connector

In each of the following Examples and Comparative Example, a plurality of valve bodies were produced.

Example 1

First, a plate-shaped base material composed of a silicone rubber and provided with a first slit and a second slit was prepared.

Next, the upper and lower surfaces of the base material were each irradiated with a laser beam through a photomask under the following irradiation conditions.

<Laser Beam Irradiation Conditions>
Laser beam source: Fluorine laser
Laser beam wavelength: 157 nm
Formation density of beam-transmitting parts in photomask: 1000 pieces/mm2
Proportion (beam transmission factor) of beam-transmitting parts: 20% to 70%
Pattern of beam-transmitting parts: Grid The valve bodies were produced in the above-mentioned manner.

Next, connectors as shown in FIG. 1 fitted with these valve bodies were produced.

Then, one of the plurality of valve bodies obtained as above was cut, and the cut surface was observed under a scanning electron microscope. That is, the valve body is cut vertically relative to the illustration in FIG. 2 so that a cross-section of the protrusions or hemispherically projecting parts 7b, 7c can be seen.

As a result, a multiplicity of hemispherical projected parts (surface layers) projecting from the surface of the base material were observed to be present selectively and spaced apart in the regions irradiated with the laser beam. The projecting height of the projected parts was measured to be 1 μm.

Further, the cut surface was subjected to elemental analysis. It was found that the valve body had a main body part (corresponding to the main body part 7a in FIG. 3) composed of a silicone rubber, and a surface layer(s) (corresponding to the surface layer(s) 7b in FIG. 3) provided on the surface of the main body part and composed of silicon oxide.

In addition, distributions of carbon and oxygen in the cut surface were analyzed by elemental mapping analysis. Then, the thicknesses of the surface layer and an intermediate layer (corresponding to the intermediate layer 7c in FIG. 3) of the valve body were estimated, taking into account the facts that the content of carbon in the silicone rubber was high, that the content of oxygen in silicon oxide was high whereas the content of carbon was approximately zero, etc.

As a result, the thickness of the surface layer was estimated at about 1.5 μm, and the thickness of the intermediate layer at about 0.5 μm.

Example 2

Valve bodies and connectors fitted with the valve bodies were produced in the same manner as in Example 1 above, except that the use of the photomask was omitted, and the upper and lower surfaces of a base material were entirely irradiated with a laser beam.

A surface layer spreading in a surface form was observed on the surfaces of the base material.

In addition, elemental mapping analysis of a cut surface was carried out in the same manner as in Example 1, whereon the presence of an intermediate layer was confirmed.

Example 3

First, a plate-like base material composed of a silicone rubber and provided with a first slit and a second slit was prepared. Next, silicon oxide was vapor deposited on each of upper and lower surfaces of the base material. In this manner, valve bodies were produced.

Thereafter, connectors shown in FIG. 1 fitted with the valve bodies were produced.

Example 4

First, a plate-like base material composed of a silicone rubber and provided with a first slit and a second slit was prepared. Next, silicon was vapor deposited on each of the upper and lower surfaces of the base material.

Subsequently, each of the silicon films thus obtained was irradiated with UV rays in the presence of ozone. This resulted in oxidation of the silicon films and, hence, modification thereof into silicon oxide. In this manner, valve bodies were produced.

Thereafter, connectors shown in FIG. 1 fitted with the valve bodies were produced.

Comparative Example

Valve bodies and connectors were produced in the same manner as in Example 1 above, except that the base material used in Example 1 was directly used as the valve body. A silicone oil was applied to the valve body as a lubricating liquid.

2. Evaluation 2.1 Evaluation of Sliding Properties

Ten connectors each obtained in each of the Examples and the Comparative Example described above were evaluated to assess the sliding properties, in the manner described below. In the following measurement of sliding resistance, measurement of the sliding resistance was carried out for each of five connectors not having been subjected to an EB sterilizing treatment and for five connectors having been subjected to the EB sterilizing treatment, and average of the measured values for the five connectors was used as an object of evaluation.

<1> First, ten connectors produced as above and guiding catheters (produced by Terumo Corporation) of 5 Fr in size were prepared.

Then, five connectors were subjected to an EB sterilizing (electron beam sterilizing) treatment, whereas the remaining five connectors were subjected to an EOG sterilizing (ethylene oxide gas sterilizing) treatment instead of being subjected to the EB sterilizing treatment. The intensity (absorption dose) of the electron beam used in the EB sterilization was 40 kGy.

<2> Next, the catheter was inserted in the valve body of the produced connectors.

<3> Subsequently, the cap body of the connector was rotated to the limit of rotating operation, thereby fastening (fixing) a tube with the valve body.

<4> Thereafter, in this condition, the sliding resistance in pulling out the catheter was measured. In measurement of the sliding resistance, the pulling-out amount of the catheter was 100 mm, and the pulling-out rate was 100 mm/min. Loads exerted on the catheter at the times of insertion and pulling-out were measured on an autograph. In this manner, an initial sliding resistance (unit: gf) was obtained.

<5> Next, a series of processes of inserting the catheter into the valve body of the connector and pulling out the catheter from the valve body of the connector was repeated 50 times in water.

<6> Then, the connector and the catheter were taken out of water, and the sliding resistance at the time of insertion and pulling-out of the catheter in relation to the connector was measured in the same manner as in <4> above. In this way, a sliding resistance value (unit: gf) after 50 reciprocal slides was obtained.

The results of the above measurements are shown in Table 1 and FIG. 8. FIG. 8 does not include evaluation results for Example 4 because when it came time to test and evaluate this Example, the equipment was not available for testing purposes.

Referring to Table 1, first, in the condition where the EB irradiation was yet to be conducted, the evaluation results of each of the Examples and the evaluation results of the Comparative Example were compared.

The evaluation results show that for the connectors obtained in each of the Examples, the sliding resistance after 50 times of sliding showed a lowering rather than an increase as compared with the initial sliding resistance, notwithstanding that a lubricating liquid was not used. On the other hand, for the connectors obtained in the Comparative Example, the sliding resistance after 50 times of sliding showed a large increase as compared with the initial sliding resistance. It is thought that this may arise from a lowering in lubricity because of gradual leaning of the lubricating liquid attendant on the reciprocal sliding of the catheter. In other words, it is surmised that in the cases of the connectors obtained in each of the Examples, such a lowering in lubricity did not occur because no lubricating liquid was used.

In addition, a comparison between Example 1 and Example 2 shows that the connectors obtained in Example 1 showed a lower sliding resistance. This is considered to be due to the difference in the area of contact between the valve body of the each of connector and the catheter.

In the condition after the EB irradiation, the evaluation results of each of Examples and evaluation results of Comparative Example were compared.

The evaluation results show that the sliding resistance values of the connectors obtained in each of the Examples were lower than the sliding resistance values of the connectors obtained in the Comparative Example, both initially and after 50 times of sliding. It is thought hat this result may arise from the fact that the valve bodies obtained in each of the Examples were superior to the valve bodies obtained in Comparative Example in electron beam resistance (radiation resistance) and so the valve body was inhibited or prevented from being altered or deteriorated by EB irradiation.

Next, for the connectors obtained in each of the Examples and the Comparative Example, the evaluation results in the condition where EB irradiation was yet to be conducted and the evaluation results in the condition after the EB irradiation were compared. Here, it is seen that in the cases of the connectors obtained in each of the Examples, the increase in the amount of the initial sliding resistance attendant on the EB irradiation was suppressed to a comparatively low level respectively (see the arrows in FIG. 8). From this result, it can be seen that the connectors obtained in each of the Examples are less liable to yield an increase in sliding resistance values even when subjected to a sterilizing treatment by EB irradiation and, hence, it can be said that they are medical instruments capable of realizing relatively high operability while securing safety.

On the other hand, the connectors obtained in the Comparative Example showed a relatively large increase in sliding resistance value attendant on EB irradiation (see the arrow in FIG. 8). It is surmised that this arises from alteration and/or deterioration of the valve bodies obtained in the Comparative Example, under the influence of the EB (electron beam) sterilizing. Based on this, it can be said that the connectors obtained in the Comparative Example may yield an increase in sliding resistance value when subjected to a sterilizing treatment by EB irradiation.

The valve body disclosed here is a valve body having an opening/closing part which opens or closes while sliding on an inserted member. The valve body is characterized in that at least the opening/closing part includes a main body part composed of a silicone rubber, and a surface layer provided at least in an area on a surface of the main body part and constituted of silicon oxide. Therefore, it is possible to obtain a valve body which shows a sliding resistance exerted on the member less liable to increase even upon an increase in the number of times of sliding of the member to be inserted in the opening/closing part and which is excellent in radiation resistance and liquid-tightness, In addition, the configuration in which a plurality of surface layers in the shape of dots are dispersed on a surface of the main body part promises a reduction in sliding resistance, with little loss of mechanical characteristic properties such as flexibility and elasticity of the silicone rubber. Accordingly, the valve body can exhibit, to a relatively high extent, both excellent sliding properties on a member to be inserted and high liquid-tightness. Furthermore, the structure in which the surface layers in the form of dots are provided in the manner of projecting from the surface of the main body part reduces the area of the surface where the valve body slides on the member inserted in the valve body. This helps facilitate a further reduction in the sliding resistance exerted on the member.

The detailed description above describes embodiments of a valve body disclosed here, including processes for producing the valve body and a medical instrument embodying the valve body. It is to be understood that the invention is not limited to the precise embodiments and variations described above and illustrated in the drawing figures. Various changes, modifications and equivalents cab be implemented by one skilled in the art without departing from the spirit and scope of the invention as defined in the appended claims. It is expressly intended that all such changes, modifications and equivalents falling within the scope of the claims are embraced by the claims.

What is claimed is:

1. A process for producing a valve body comprising an opening/closing part which opens upon inserting a member into the opening/closing part and which closes upon withdrawing the member from the opening/closing part, the process comprising:
   forming a surface layer comprised of silicon oxide at least in a region that includes the opening/closing part;
   wherein the surface layer is comprised of silicon oxide formed on a surface of a base material, the base material comprising a silicone rubber; and
   wherein the forming of the surface layer of silicon oxide comprises irradiating at least a region of a surface of the opening/closing part with a laser beam so that the silicone rubber in the region is modified into silicon oxide and raised.

2. The process for producing the valve body according to claim 1, wherein the laser beam has a wavelength of not more than 200 nm.

3. The process for producing the valve body according to claim 1, wherein the irradiating with the laser beam comprises directing the laser beam through a photomask having a window part of a predetermined shape, the irradiation of the surface layer of silicone rubber with the laser beam modifying the silicone rubber into silicon oxide in the region having a shape corresponding to the predetermined shape.

4. The process for producing the valve body according to claim 3, wherein the photomask is comprised of a mesh-shaped member or a punching metal.

5. The process for producing the valve body according to claim 1, wherein the surface layer is formed by forming a layer of silicon oxide at least in a region of a surface of the opening/closing part.

6. A process for producing a valve body comprising an opening/closing part which opens upon inserting a member into the opening/closing part and which closes upon withdrawing the member from the opening/closing part, the process comprising:
   forming a surface layer comprised of silicon oxide at least in a region that includes the opening/closing part;

wherein the surface layer is comprised of silicon oxide formed on a surface of a base material, the base material comprising a silicone rubber;

wherein the surface layer is formed by forming a layer of silicon oxide at least in a region of a surface of the opening/closing part; and wherein the forming of the surface layer of silicon oxide comprises irradiating at least a region of a surface of the opening/closing part with a laser beam.

7. The process for producing the valve body according to claim 6, wherein the laser beam has a wavelength of not more than 200 nm.

8. The process for producing the valve body according to claim 6, wherein the irradiating with the laser beam comprises directing the laser beam through a photomask having a window part of a predetermined shape, the irradiation of the surface layer of silicone rubber with the laser beam modifying the silicone rubber into silicon oxide in the region having a shape corresponding to the predetermined shape.

9. The process for producing the valve body according to claim 8, wherein the photomask is comprised of a mesh-shaped member or a punching metal.

10. A process for producing a valve body comprising an opening/closing part which opens upon inserting a member into the opening/closing part and which closes upon withdrawing the member from the opening/closing part, the process comprising:

forming a surface layer comprised of silicon oxide at least in a region that includes the opening/closing part;

wherein the surface layer is comprised of silicon oxide formed on a surface of a base material, the base material comprising a silicone rubber; and wherein the surface layer is formed by forming a silicon layer at least in a region on a surface of the opening/closing part, and thereafter subjecting the silicon layer to an oxidizing treatment so as to modify silicon into silicon oxide.

11. The process for producing the valve body according to claim 10, wherein the forming of the surface layer of silicon oxide comprises irradiating at least a region of a surface of the opening/closing part with a laser beam.

12. The process for producing the valve body according to claim 11, wherein the laser beam has a wavelength of not more than 200 nm.

13. The process for producing the valve body according to claim 11, wherein the irradiating with the laser beam comprises directing the laser beam through a photomask having a window part of a predetermined shape, the irradiation of the surface layer of silicone rubber with the laser beam modifying the silicone rubber into silicon oxide in the region having a shape corresponding to the predetermined shape.

14. The process for producing the valve body according to claim 13, wherein the photomask is comprised of a mesh-shaped member or a punching metal.

15. The process for producing the valve body according to claim 10, wherein the surface layer is formed by forming a layer of silicon oxide at least in a region of a surface of the opening/closing part.

* * * * *